United States Patent
Cruise (10) Patent No.: US 7,201,918 B2
(45) Date of Patent: Apr. 10, 2007

(54) COMPOSITIONS, SYSTEMS AND METHODS FOR TREATMENT OF DEFECTS IN BLOOD VESSELS

(75) Inventor: Gregory M. Cruise, Rancho Santa Margarita, CA (US)

(73) Assignee: Microvention, Inc., Aliso Viejo, CA (US)

( * ) Notice: Subject to any disclaimer, the term of this patent is extended or adjusted under 35 U.S.C. 154(b) by 158 days.

(21) Appl. No.: 10/990,942

(22) Filed: Nov. 16, 2004

(65) Prior Publication Data

US 2006/0105014 A1 May 18, 2006

(51) Int. Cl.
*A61F 2/00* (2006.01)
*A61K 35/14* (2006.01)
*A61M 31/00* (2006.01)

(52) U.S. Cl. .................... 424/423; 424/529; 604/508; 604/509

(58) Field of Classification Search ..................... None
See application file for complete search history.

(56) References Cited

U.S. PATENT DOCUMENTS

| | | | |
|---|---|---|---|
| 4,551,132 A | 11/1985 | Pasztor et al. | |
| 4,795,741 A | 1/1989 | Leshchiner et al. | |
| 4,819,637 A | 4/1989 | Dormandy et al. | |
| 5,122,136 A | 6/1992 | Guglielmi et al. | |
| 5,525,334 A | 6/1996 | Ito et al. | |
| 5,580,568 A | 12/1996 | Greff et al. | |
| 6,562,362 B1 * | 5/2003 | Bae et al. | 424/425 |
| 6,602,261 B2 | 8/2003 | Greene et al. | |
| 6,808,518 B2 * | 10/2004 | Wellman et al. | 604/507 |
| 6,878,384 B2 | 4/2005 | Cruise et al. | |
| 6,887,974 B2 | 5/2005 | Pathak | |
| 7,014,645 B2 | 3/2006 | Greene, Jr. et al. | |
| 2005/0004660 A1 | 1/2005 | Rosenbluth et al. | |
| 2005/0060017 A1 | 3/2005 | Fischell et al. | |
| 2005/0133046 A1 | 6/2005 | Becker et al. | |
| 2005/0245893 A1 * | 11/2005 | Leschinsky | 604/509 |
| 2005/0276863 A1 | 12/2005 | LeTort | |
| 2005/0287189 A1 | 12/2005 | Noujaim et al. | |

* cited by examiner

*Primary Examiner*—Sandra E. Saucier (57) ABSTRACT

Methods and systems are provided for treating a vascular structure having a defect, for example, a cerebral artery having a weakened wall that has formed an aneurysm. The methods include substantially entrapping a quantity of blood within a vascular defect, and introducing a quantity of a crosslinking agent, for example as a liquid solution, into the entrapped blood. The crosslinking agent is a compound in which each molecule of the compound has at least two nucleophilic-reactive functional groups. The crosslinking agent is allowed to combine with and react with the substantially entrapped blood, and a substantially solid mass made of crosslinked blood is formed within the defect.

47 Claims, 5 Drawing Sheets

COMPOSITIONS, SYSTEMS AND METHODS FOR TREATMENT OF DEFECTS IN BLOOD VESSELS

FIELD OF THE INVENTION

The present invention generally relates to medical treatment methods, and more specifically relates to methods, compositions and systems useful in treatment of aneurysms and other defects in vascular structures.

BACKGROUND OF THE INVENTION

Many catheter-based endovascular interventional procedures have become common. For example, angioplasty and stenting are used to treat cardiac, peripheral and neurovascular disease. Stent-grafting is used to treat thoracic and abdominal aortic aneurysms. Also, endovascular embolization has been used to control vascular bleeding, to occlude the blood supply to tumors, and to occlude vascular aneurysms, particularly intracranial aneurysms. Typically, in embolization procedures intended to treat cerebral aneurysms, platinum coils are used to occlude vascular structures throughout the body, including vascular aneurysms.

Vascular aneurysms are produced when a thinning or weak region in a vessel wall dilates, eventually posing a health risk from its potential to rupture. While aneurysms can occur in any blood vessel, most occur in the aorta and cerebral arteries. The etiology of aneurysm formation is not entirely understood, but is thought to be related to effects of fluid dynamics, atherosclerotic vessel degeneration, vessel trauma, infection, smoking, high blood pressure, and other causes leading to vessel degeneration. Left untreated, aneurysms may lead to gradual vessel expansion, thrombus formation leading to stroke or other vessel blockage, vessel rupture, shock, and eventual death.

Several different treatment modalities have been employed in the endovascular occlusion of vascular aneurysms. For example, U.S. Pat. No. 4,819,637 to Dormandy, Jr. et al., the entire disclosure of which is incorporated herein by this reference, describes a vascular embolization system that employs a detachable balloon delivered to the aneurysm site by an intravascular catheter. The balloon is carried into the aneurysm at the tip of the catheter and is inflated inside the aneurysm with a solidifying fluid (typically a polymerizable resin or gel) to occlude the aneurysm. The balloon is then detached from the catheter by gentle traction on the catheter. While the balloon-type embolization device, such as described in Dormandy, Jr. et al, can provide an effective occlusion of many types of aneurysms, the device can be difficult to retrieve or move after the solidifying fluid has set. In addition, the device is difficult to visualize. Furthermore, there are risks of balloon rupture during inflation and of premature detachment of the balloon from the catheter.

In recent years, detachable platinum coils have become widely used to treat cerebrovascular structures such as aneurysms, fistulae, arterio-venous malformations, and vessels. Platinum coils induce blood stasis and thrombus formation in the vascular structure. In some structures, the platinum coils achieve the desired patient outcomes. For example, in small aneurysms with small necks, platinum coils are extremely efficacious. However, in aneurysms that are large, wide-necked, or fusiform, the outcomes of platinum coils are not optimal. In particular, some of these devices, for example, such as devices disclosed in Guglielmi, et al., U.S. Pat. No. 5,122,136, the entire disclosure of which is incorporated herein by this reference, have a secondary configuration such as a helix or some similar form. These devices form a three-dimensional non-minimum energy state configuration when deployed inside an aneurysm; however, they have displayed a tendency to revert to their minimum energy state configurations over time. This, in turn, results in compaction due to "coin stacking" (i.e., returning to the secondary helical configuration), thereby allowing recanalization of the aneurysm.

A further development has been described in Greene et al., U.S. Pat. No. 6,602,261, the entire disclosure of which is incorporated herein by this reference. Greene et al. describe an embolization device that includes one or more expansible, hydrophilic embolizing elements non-releasably carried along the length of a filamentous carrier.

Another approach is the direct injection of a liquid polymer embolic agent into the vascular site to be occluded. One type of liquid polymer used in the direct injection technique is a rapidly polymerizing liquid, such as a cyanoacrylate resin, particularly isobutyl cyanoacrylate, that is delivered to the target site as a liquid, and then is polymerized in situ. Alternatively, a liquid polymer that is precipitated at the target site from a carrier solution has been used. An example of this type of embolic agent is a cellulose acetate polymer mixed with bismuth trioxide and dissolved in dimethyl sulfoxide (DMSO). Another type is ethylene vinyl alcohol dissolved in DMSO. On contact with blood, the DMSO diffuses out, and the polymer precipitates out and rapidly hardens into an embolic mass that conforms to the shape of the aneurysm. Other examples of materials used in this "direct injection" method are disclosed in U.S. Pat. No. 4,551,132 to Pasztor et al.; U.S. Pat. No. 4,795,741 to Leshchiner et al.; U.S. Pat. No. 5,525,334 to Ito et al.; and U.S. Pat. No. 5,580,568 to Greff et al. The disclosure of each document cited herein is incorporated herein in its entirety by this reference.

Despite these advances in the capabilities of embolization materials, more effective methods of treating a defect in a vascular structure are needed, wherein the methods can be easily accomplished using a catheter, for example a microcatheter, have reduced risk of emboli, and allow formation of a structure amenable to physiological healing responses. The present invention provides such methods and systems or kits for performing such methods, the methods and systems being useable in various applications, including, but not limited to, medical implant applications wherein the material is used as or in conjunction with aneurysms, fistulae, arterio-venous malformations, vessel occlusions, and other vascular structures.

SUMMARY OF THE INVENTION

Accordingly, the present invention provides new methods and systems for treating a defect in a vascular structure, the defect being for example, but not limited to, an aneurysm, for example, a cerebral aneurysm, an arterio-venous malformation, a cut, tear, perforation or other opening in the wall of a vascular structure, or other vascular defect that can be treated using the methods and systems of the present invention.

In a broad aspect of the present invention, methods are provided for treating a medical condition of a human or veterinary patient, for example, in order to treat a defect in a vascular structure, wherein the methods generally comprise the steps of introducing a crosslinking agent into a target location within the body of the patient and allowing the crosslinking agent to combine with blood and react with the blood to form a substantially solid mass. Accordingly, there are provided methods for treating various diseases, conditions, malformations, or disorders of human or veterinary patients by introducing (for example, injecting, instilling, infusing or otherwise introducing, for example, through a cannula, catheter, microcatheter, needle or other introduction device) a crosslinking agent, specifically a crosslinking agent, into a vascular structure, and allowing the crosslinking agent to react with blood in the vascular structure. In these methods of the present invention, the reaction between the blood and the crosslinking agent results in the formation of a substantially solid mass within the vascular structure, for example within a defect in the vascular structure. The substantially solid mass can be described as a crosslinked network amenable to healing and remodeling by the physiological healing processes into stable fibrous connective tissue.

The present methods may be used in place of conventional endovascular treatments for, such as for example, vascular embolization utilized as a means of treating or controlling vascular bleeding, occluding the blood supply to a tumor, occluding vascular aneurysms, for example but not limited to intracranial aneurysms.

A crosslinking agent useful in the methods of the present invention may include a crosslinking agent that includes a compound wherein each molecule of said compound has at least two nucleophilic-reactive functional groups, more preferably, has at least three nucleophilic-reactive functional groups, which may depend on the specific medical application of the invention. The molecular structure of such compound may comprise a core portion (e.g., a molecular backbone) and a plurality of nucleophilic-reactive functional groups. In some embodiments of the present invention, the core portion may be water soluble and may have at least two chemical groups suitable for derivatization to form or attach the functional groups. The core portion of the compound may comprise a straight or branched, chiral or nonchiral, cyclic or noncyclic, small molecule, and may be selected from pentaerythritol, di(pentaerythritol), nitriloacetic acid, glycerol, ethylene glycol, trimethylol propane, di(trimethylol propane), polyacids, heptanedioic acid, octanedioic acid, hexadecanedioic acid, multi-functional aromatic compounds, phloroglucinol, 1,2,4-benzene triol and pyrogallol. Each functional group may be independently selected from electrophilic groups, esters, N-hydroxysuccinimide esters, vinyl sulfones, N-ethyl maleimides, iodoacetamides, ortho-pyridyl disulfides, aldehydes, sulfonyl chloride, aryl halides, epoxides, active esters, carbonyldiimidazoles, nitrophenyl carbonates, tresylates, tosylates, mesylates, and isocyanates.

The small molecule is coupled to at least one branched or unbranched polymer and may be water soluble. The polymer may be selected from: poly(ethylene glycol), poly(ethylene oxide), poly(vinyl alcohol), poly(propylene glycol), poly(ethylene oxide)-co-poly(propylene oxide), poly(vinyl pyrrolidinone), poly(amino acids), dextrans, poly(ethyloxazoline), polysaccharides, proteins, glycosaminoglycans, and carbohydrates.

The crosslinking agent may comprise at least one compound selected from: ethoxylated trimethylol propane succinimidyl succinate, ethoxylated pentaerythritol succinimidyl succinate, 4-arm poly(ethylene glycol) succinimidyl succinate, 4-arm poly(ethylene glycol) succinimidyl succinate, and ethoxylated phloroglucinol succinimidyl succinate.

In accordance with some methods of the present invention, the crosslinking agent is introduced subcutaneously, in a wound, in a tumor or blood vessels that supply blood to the tumor, in an organ, in an aberrant blood vessel or vascular structure, in a space located between or among tissues or anatomical structures or within a surgically created pocket or space. In this manner, the methods of the present invention are useful for the treatment of aneurysms, fistulae, arterio-venous malformations, vessel occlusions, and other medical conditions.

In a more specific aspect of the present invention, a method is provided for treating a vascular defect such as an aneurysm, wherein the vascular defect has an inner cavity and an opening that extends through the wall of the vascular structure and into the inner cavity. In such a vascular defect, at least some blood flowing through the lumen of the vascular structure may enter the inner cavity through the opening. The method in accordance with the invention may comprise the step of substantially sealing the inner cavity to substantially entrap a quantity of blood therein. More specifically, this sealing step may comprise positioning a blocking member, such as an expandable member, for example a balloon, adjacent to the opening to substantially seal the defect thereby entrapping the quantity of blood within the inner cavity. More specifically, for example, the step of positioning a blocking member comprises advancing an expandable blocking member through the lumen of the vascular structure to a position adjacent to the defect while the expandable blocking member is in a substantially unexpanded configuration, and thereafter, expanding the expandable member such that it substantially seals the defect thereby entrapping a quantity of blood within the defect.

The method further comprises introducing the crosslinking agent into the substantially entrapped quantity of blood, for example by means of a catheter inserted through the opening into the inner cavity of the defect, and allowing the crosslinking agent to react, thereby forming a substantially solid mass within the inner cavity. The blocking member may then be removed from the vascular structure after the crosslinking agent has been introduced, for example after the substantially solid mass has formed within the inner cavity.

In accordance with other embodiments of the present invention, the vascular defect may comprise a cut, tear, perforation or other opening in the wall of the vascular structure.

The blocking member may be formed integrally of, or may be attached to the catheter used to introduce the crosslinking agent. Alternatively, the blocking member is a separate component from the catheter used to introduce the crosslinking agent.

Optionally, the crosslinking agent used in the methods and systems of the present invention may combined with a visualization enhancing agent. For example, the crosslinking agent may be rendered radiopaque for visualization under radiographic imaging. The crosslinking agent may be combined with radiopaque particles (e.g., tantalum, gold, platinum, barium and other heavy metals etc.) so as to impart radiopacity to the entire crosslinking agent.

Alternatively or additionally, the crosslinking agent may be made to have magnetic properties that allow it to be imaged by magnetic resonance. For example, the crosslinking agent may be combined with particles of gadolinium and gadolinium-containing compounds.

In some embodiments of the invention, the crosslinking agent is combined with an effective amount of a solvent, for example, one of saline, phosphate buffered saline, and dimethysulfoxide, a surfactant, for example, one of N-lauroyisarcosine, lauryl sulfate, and Triton X-100, and or may be combined with a biologically active substance that is effective to enhance and/or modify a biological response within or near the defect, for example, but not limited to a substance is selected from: therapeutic agents, drugs, prodrugs, pharmaceuticals, proteins, cells, genetically modified cells, gene therapy preparations comprising genes and vectors, growth factors, fibroblast growth factors, platelet derived growth factors, insulin like growth factor, bone morphogenic proteins, inhibins, growth differentiating factors, activins, epidermal growth factors, vascular endothelial growth factors, connective tissue activated peptides, osteogenic factors and fragments, analogs, derivatives of growth factors, autograft cells or tissue, allograft cells or tissue, xenograft cells or tissue, naturally occurring cells or tissue, genetically modified cells or tissue, differentiated cells, non-differentiated cells, stem cells, cells that promote the formation or ingrowth of fibrous connective tissue, substances that promote the formation or ingrowth of fiberous connective tissue.

In some embodiments of the invention, the crosslinking agent is dispersed or dissolved in a solvent and is further combined with at least one other of i) a visualization enhancing agent, ii) a surfactant, and iii) a biologically active substance.

Another aspect of this invention is to provide a multifunctional crosslinking agent and methods of preparation and use.

Methods for occluding a blood vessel or vascular site are described herein and also form and aspect of this invention. In certain embodiments, a fluid crosslinker, for example a liquid crosslinking agent, is infused with the aid of a balloon catheter and a mixing coil. In other embodiments, the infusion is done after deployment of a flow-disrupting device either within the vascular site of in a blood vessel adjacent to the site (e.g. the parent vessel adjacent an aneurysm).

In yet another aspect of the invention, a kit is provided for treating a vascular defect, for example, the kit comprising a catheter structured to be introduced into a vascular structure having a defect; and a quantity of a crosslinking agent effective to react and form a substantially solid mass within the defect. The kit may further comprise a blocking member suitably sized and structured for substantially sealing the defect to substantially entrap a quantity of blood within the defect.

Further aspects of this invention will be come apparent to those of skill in the art upon reference to the accompanying Drawings and upon reading of the detailed description of exemplary embodiments set forth herein.

DETAILED DESCRIPTION

The following detailed description and examples are provided for the limited purpose of illustrating exemplary embodiments of the invention and not for the purpose of exhaustively describing all possible embodiments of the invention.

Methods are provided for treating human or veterinary patients which generally comprise introducing a crosslinking agent into a target area of a human or veterinary patient and allowing the crosslinking agent to combine and react with blood in the target area thereby forming a substantially solid mass in situ. This substantially solid mass provides a crosslinked network that can be penetrated, remodeled, and/or degraded by myofibroblasts and other components of the healing process.

The crosslinking agent generally comprises a compound in which each molecule of the compound comprises a core portion and a plurality of nucleophilic-reactive functional groups. Typically, the core portion comprises a compound that is water soluble and has at least two chemical groups suitable for derivatization. The core portion of the compound is a straight or branched, chiral or nonchiral, cyclic or noncyclic, small molecule.

For example, the crosslinking agent comprises a core molecule is non-toxic, biologically-inert, water soluble, and has at least two, more preferably at least three, chemical groups suitable for derivatization. Examples of suitable small molecule cores include pentaerythritol, di(pentaerythritol), nitriloacetic acid, glycerol, ethylene glycol, trimethylol propane, di(trimethylol propane), polyacids, (i.e. heptanedioic acid, octanedioic acid, and hexadecanedioic acid), and multi-functional aromatic compounds (i.e. phloroglucinol, 1,2,4-benzene triol, and pyrogallol). The preferable small molecule cores are trimethylol propane, glycerol, and phloroglucinol.

The coupling of water soluble polymers may enhance the water solubility of the small molecule core. Examples of suitable polymeric include poly(ethylene glycol), poly(ethylene oxide), poly(vinyl alcohol), poly(propylene glycol), poly(ethylene oxide)-co-poly(propylene oxide), poly(vinyl pyrrolidinone), poly(amino acids), dextrans, poly(ethyloxazoline), polysaccharides, proteins, glycosaminoglycans, and carbohydrates. The polymers include poly(ethylene glycol) and poly(propylene glycol).

Additionally the core may be modified, for example chemically modified, in order to permit visualization of the crosslinking agent, for example by means of fluoroscopy or magnetic resonance imaging. Examples of suitable agents for visualization under fluoroscopy include iodinated molecules and certain heavy metals, including tantalum and barium. In some embodiments of the invention, the crosslinking agent is combined with iodinated aromatic core molecules (i.e. iodinated phloroglucinol) to permit fluoroscopic imaging. Examples of suitable agents for visualization under magnetic resonance imaging include gadolinium compounds.

The crosslinker may have at least two, and in some cases at least three, electrophilic groups to react with nucleophilic groups that may be present in the blood. Examples of electrophilic groups suitable include vinyl sulfones, N-ethyl maleimides, iodoacetamides, orthopyridyl disulfides, aldehydes, sulfonyl chloride, aryl halides, epoxides, active esters, carbonyldiimidazoles, nitrophenyl carbonates, tresylates, tosylates, mesylates, and isocyanates. The preferable electrophilic groups are active esters, more preferably N-hydroxysuccinimide esters.

The crosslinking agent is preferably provided in a form that enables introduction into the body by means of a catheter, for example a microcatheter. Thus, in embodiments of the invention in which the crosslinker component is available as a solid material, the crosslinking agent may be made into a solution by combining the crosslinker with a suitable solvent. For example, for a water-soluble crosslinker, 0.9% saline is a suitable solvent. A suitable solvent for an organic soluble crosslinkers, is dimethylsulfoxide.

In some embodiments of the present invention, the crosslinking agent is combined with one or more active agents, for example, biologically active agents, including pharmaceuticals, proteins, cells, genetically modified cells, and gene therapy vectors. One or more of these agents may be, can be incorporated into the crosslinker solution to modify or enhance a biological response. Non-limiting examples of active agents include transforming growth factors, fibroblast growth factors, platelet derived growth factors, insulin like growth factor, bone morphogenic proteins, inhibins, growth differentiating factors, activins, epidermal growth factors, vascular endothelial growth factors, connective tissue activated peptides, osteogenic factors and fragments, analogs, derivatives of such growth factors.

In addition, in some embodiments of the invention in which the crosslinking agent is an aqueous solution, cells may be delivered to the vascular structure. These cells may be autografts, allografts, or xenografts in nature. These cells may be naturally occurring or they may be genetically modified. Differentiated or non-differentiated cells (i.e. stem cells) may be incorporated into the crosslinker agent. For treatment of vascular structures in accordance with the invention, such cells may be selected so as to promote the formation of fibrous connective tissue.

In some embodiments of the invention, the crosslinking agent may be combined with agents effective to control a rate of formation of the substantially solid mass in situ, for example to increase or decrease the crosslinking time and/or strength of the substantially solid mass. For example, surfactants may be added to the crosslinking agent. Exemplary surfactants include N-lauroylsarcosine, lauryl sulfate, and Triton X-100.

A variety of two-part liquid agents that react to form crosslinked networks, particularly those consisting of poly (ethylene glycol) have been developed that could be used for treatment of vascular structures, in accordance with some embodiments of the present invention. U.S. Pat. Nos. 5,104,909 and 5,296,518 both to Grasel et al. disclose the formation of crosslinked networks using isocyanate and amine functionalities. U.S. Pat. No. 5,514,379 to Weissleder et al describes the formation of crosslinked structures using polymeric precursors having multiple nucleophilic and electrophilic moieties. U.S. Pat. No. 5,426,148 to Tucker discloses crosslinked networks formed between acetoacetylate and amine functionalities. U.S. Pat. No. 5,162,430 to Rhee et al. discloses a suspension of collagen mixed with a solution of a poly(ethylene glycol) derivatized with electrophilic groups forms a crosslinked network. U.S. Pat. No. 5,874,500 to Rhee et al. discloses a solution of a poly(ethylene glycol) molecule derivatized with electrophilic groups mixed with a solution of a poly(ethylene glycol) molecule derivatized with nucleophilic groups forms a crosslinked network. U.S. Pat. No. 5,583,114 to Barrows et al. and U.S. Pat. No. 6,458,147 to Cruise et al. disclose a solution of albumin mixed with a solution of poly(ethylene glycol) molecule derivatized with nucleophilic groups reacts to form a crosslinked network. U.S. Pat. No. 6,566,406 to Pathak et al discloses a solution of a small molecule and a solution of poly(ethylene glycol), one being nucleophilic and the other being electrophilic, react to form a crosslinked network. The disclosure of each document cited herein is incorporated herein in its entirety by this reference.

The methods of the present invention include the step of delivering or introducing, for example by means of a catheter or microcatheter, the crosslinking agent to the target site, for example to the defect in the vascular structure being treated. In some embodiments of the present invention, the crosslinker solution is delivered to the vascular structure endovascularly through a microcatheter with the aid of a balloon catheter. Optionally, the crosslinking agent may be volitionally mixed with blood contained within the vascular defect. Such mixing may be carried out by repeatedly advancing and retracting an object (e.g., an occlusion coil, a wire, etc.) into the vascular defect during and/or after introduction of the crosslinking agent. Alternatively, any other suitable type of mixing may be used. For example, a wire, catheter or other member may be inserted into the vascular defect and caused to vibrate (e.g., by mechanical vibration, ultrasound, etc.), thereby mixing the crosslinking agent with the blood.

Figure 1:
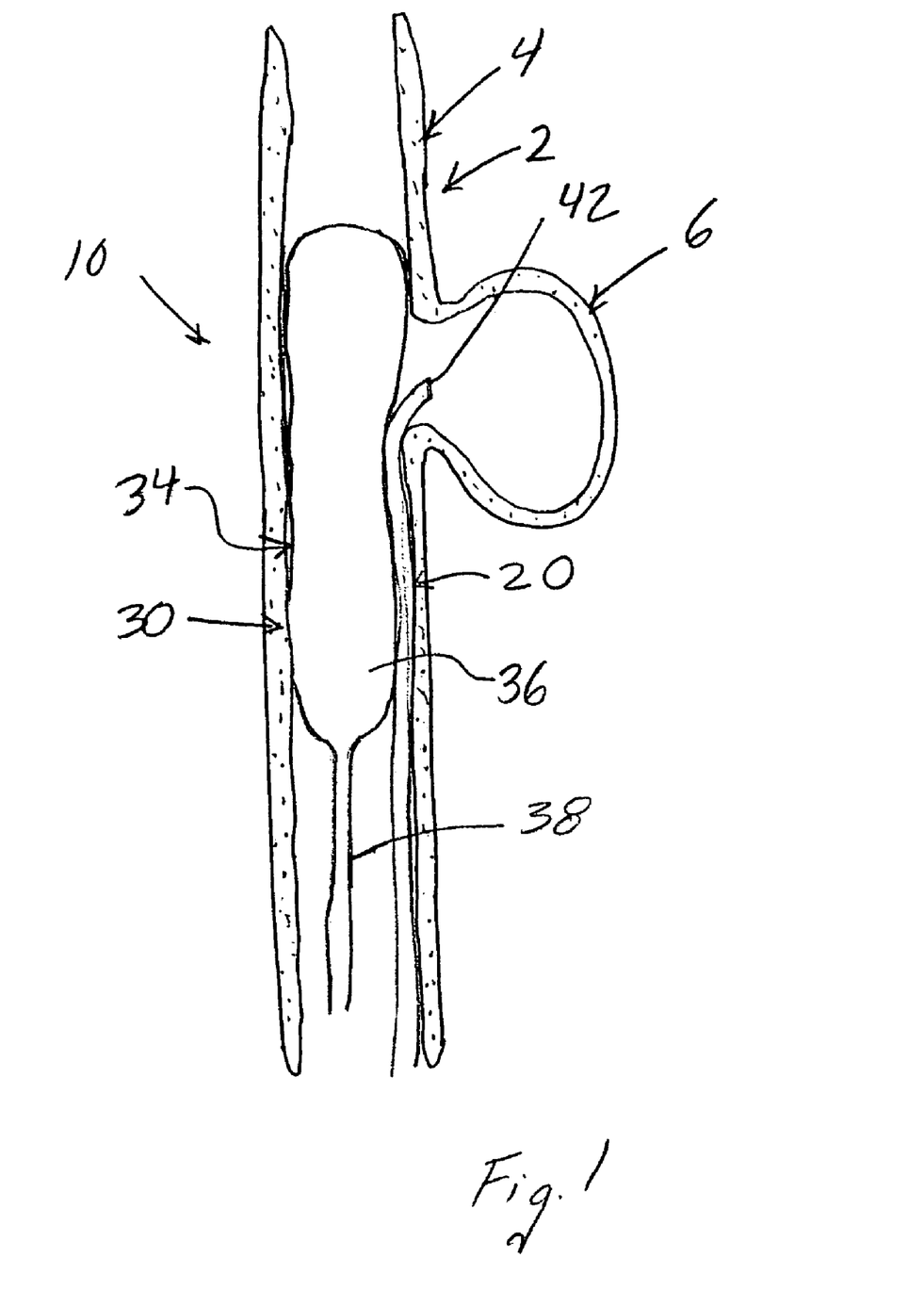
FIG. 1 shows a blocking member being used to entrap a quantity of blood within the defect in a vessel, and a microcatheter being used to deliver a crosslinking agent into the entrapped blood, in accordance with a method of the invention.

The present invention further provides a system or kit useful for treating a vascular structure having a defect. FIG. 1 illustrates a blood vessel 2 having a defect 6, and a system or kit 10 in accordance with the invention. The kit 10 generally comprises a catheter 20, for example a microcatheter, structured to be introduced into a blood vessel 2 or other vascular structure being treated, and a quantity of a crosslinking agent effective to react and form a substantially solid mass thereby treating the defect 6 in the vessel 2. The kit 10 may further comprise a blocking member 30 suitably sized and structured for substantially sealing the defect 6 to substantially entrap a quantity of blood within the defect 6.

FIG. 1 also illustrates a method in accordance with the invention. As shown, the blocking member 30 comprises, for example, a balloon catheter 34 disposed inside of a blood vessel 20 proximate the defect 6. In this illustration, the vessel 2 may be cerebral artery through which blood flows, wherein the vessel 2 includes a wall 4 having a weakened portion that has bulged to form a lesion or aneurysm 6. The balloon catheter 34 includes a flexible, expandable member 36 coupled to a catheter tube 38 effective to cause the expandable member 36 to inflate or expand within the vessel 2. In this procedure, the balloon catheter 34 is percutaneously inserted into the vasculature and advanced to the locus of the aneurysm 6. The specific size and shape of the expandable membrane 36 and catheter tube 38 may be determined a priori in order to best fit the targeted artery or blood vessel where an aneurysm has formed. The expandable member 36 is thereby inflated to appose the inner walls of the blood vessel proximate the aneurysm 6, so as to substantially isolate the aneurysm 6 and entrap a quantity of blood therein.

The microcatheter 20 is shown positioned in the vessel 2 so that a distal end 42 of the microcatheter 20 is proximate the aneurysm 6. More specifically, the distal end 42 extends adjacent or within an opening of an inner cavity of the aneurysm 6. The expandable member 36 has been expanded within the vessel 2 so as to hold or secure the microcatheter in the proper position within the vessel 2.

A fluoroscopic agent may be introduced into the site, for example through the microcatheter 20, to confirm positioning of the microcatheter 20 and to confirm isolation of the vascular structure. If appropriate, a bolus of blood may be removed or withdrawn from the aneurysm 6 in order to prevent any additional pressure against the weakened vessel wall. An appropriate quantity of a suitable crosslinking agent, such as described in detail elsewhere herein, is then introduced into inner cavity of the aneurysm 6 by means of the microcatheter 20. It is noted that the quantity of the blood bolus that had been withdrawn from the aneurysm in the earlier discussed step may be selected to be substantially equivalent to the quantity of the crosslinking agent infused into the aneurysm so as to maintain substantially equivalent pressure therein.

Figure 2:
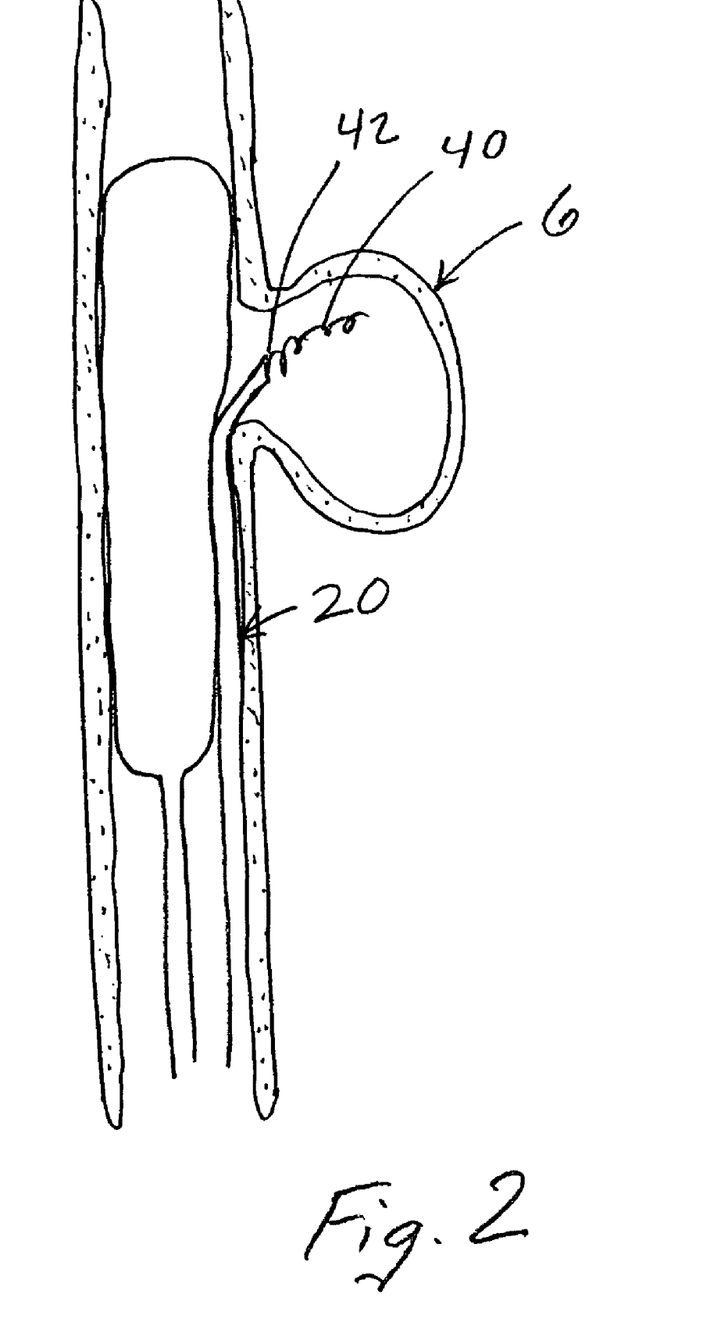
FIG. 2 shows a view similar to FIG. 1, wherein the microcatheter is being used to introduce a mixing coil into the defect to enhance mixing of the crosslinking agent with the entrapped blood.
Figure 3:
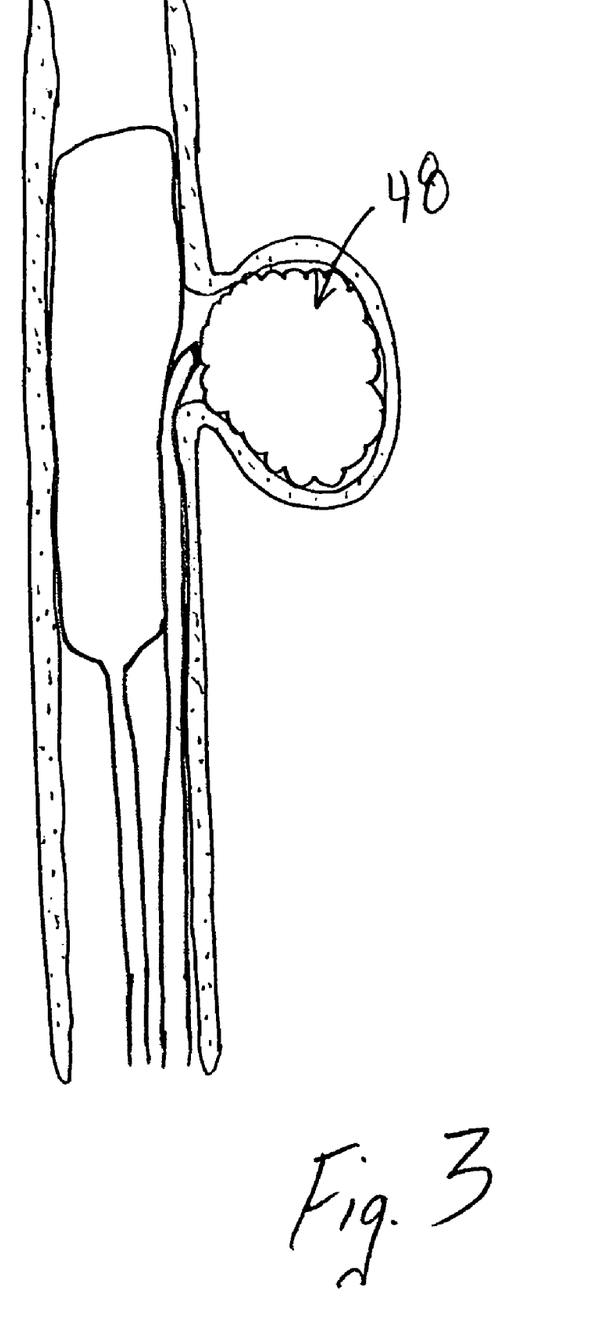
FIG. 3 shows a view similar to FIG. 1, in which a substantially solid mass has been formed within the defect, in accordance with an aspect of the invention, the mass being a result of allowing the crosslinking agent to react.
Figure 4:
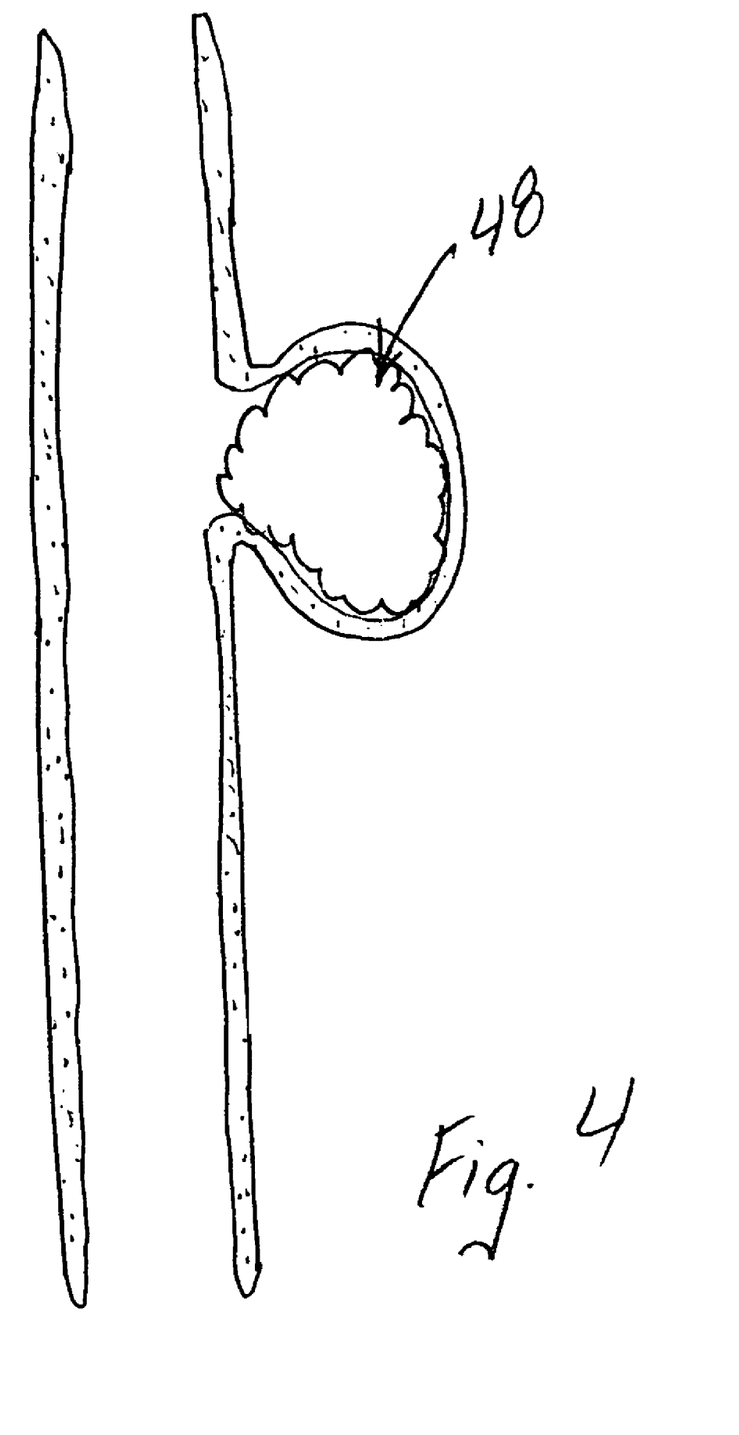
FIG. 4 shows another view of the vessel shown in FIG. 1, wherein the catheter and blocking member have now been removed from the vessel, leaving the substantially solid mass within the defect.

Turning now to FIG. 2, the crosslinking agent may be mixed into the substantially entrapped blood within the lesion 6. This may be accomplished, for example, by means of a mixing mechanism, such as a coil 40 which is passed at least once into the inner cavity, for example, through the distal end of the microcatheter 20. Examples of commercially available coils that may be used for this purpose include, but are not necessarily limited to the MicroPlex® coil system, (MicroVention, Inc., Aliso Viejo, Calif.), the Helipaq™ coil system (Micrus, Inc., Sunnyvale, Calif.) and the Guglielmi coil system (Boston Scientific, Natick, Mass.). The crosslinking agent reacts with one or more constituent(s) of the blood to form a substantially solid mass 48 within the defect 6, such as shown in FIG. 3. In a least some application of the invention, this substantially solid mass 48 may be allowed to form for a time period from about three minutes about twenty minutes. After formation of the mass 48, the expandable member 36 may be deflated, and the microcatheter 20 and blocking member 30 may then be removed or withdrawn from the site, as shown in FIG. 4.

Figure 5:
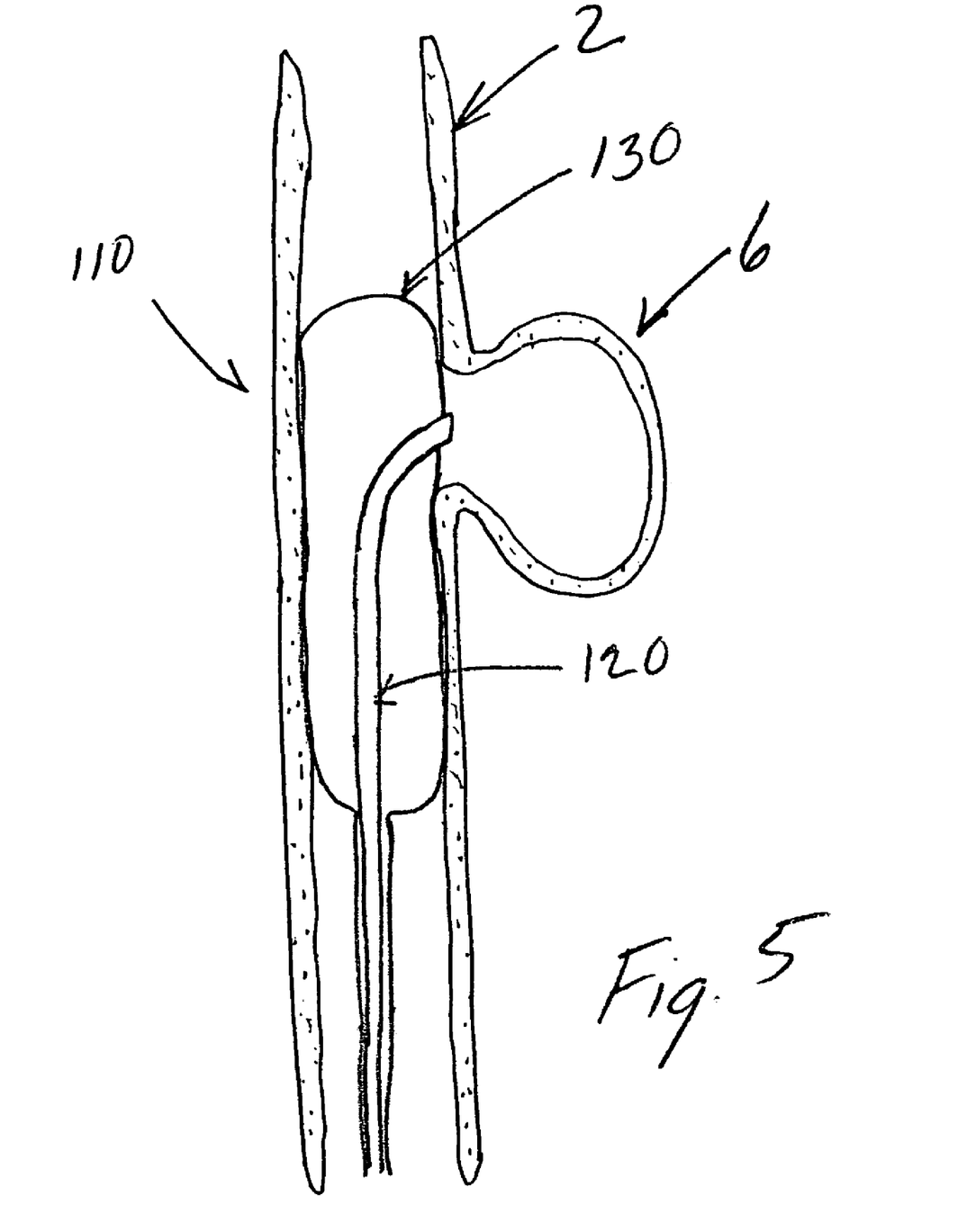
FIG. 5 shows another embodiment of the invention being used to treat a vessel having a defect.

Although the blocking member 30 and catheter 20 are shown as separate components in the FIGS. 1–4, other embodiments of the present invention may utilize a blocking member that is formed integrally with or is attached to the catheter. FIG. 5 illustrates another kit 110 in accordance with the invention being used to treat a defect 6 of a vessel 2, wherein the kit 110 comprises a quantity of a crosslinker agent, a catheter 120 for introducing the crosslinker agent into the defect 6, and blocking member 130 that is formed integrally with said catheter 120, for isolating and entrapping blood within the defect 6.

If a portion or all of the crosslinker solution enters the vasculature outside of the defect, the risk of unwanted emboli formation is low due to the nature of the crosslinker solution and relatively slow kinetics of the reaction. The flowing blood in the vasculature dilutes the crosslinker before any solid emboli can be formed.

The resulting crosslinked network is similar in structure to a thrombus formed by natural means. Naturally forming thrombus occurs through the conversion of fibrinogen to fibrin catalyzed by thrombin. Fibrinolysis occurs through the conversion of plasminogen to plasmin catalyzed by tPA. The substantially solid mass is formed through the crosslinking of blood by the crosslinker and is not susceptible to degradation via the natural fibrinolysis mechanism.

Like natural thrombus and unlike other liquid embolic agents, the substantially solid mass formed by methods and systems of the present invention immediately provides a crosslinked network that can be penetrated, remodeled, and degraded by myofibroblasts and other components of the healing process. This healing process transforms the virtually acellular synthetic thrombus into fibrous connective tissue, marked by myofibroblasts in a collagen extracellular matrix. Macrophages and other components of the healing process phagocytose the degraded synthetic thrombus.

The following are examples of some of the biomedical applications of crosslinkers to form the substantially solid mass as described above. It will be appreciated, however, that this crosslinked network material has many other medical and non-medical applications in addition to the specific examples set forth herein.

EXAMPLE 1

Preparation of a Sample Crosslinking Agent, Trimethylol Propane 20/3

Ethoxylated trimethylol propane 20/3 (20 g, Aldrich) is dissolved in xylene. The water is removed from the system by azeotropic distillation. Succinic anhydride (8.1 g, Aldrich) and pyridine (100 mL, Aldrich) were added. The reaction is allowed to proceed under reflux overnight. The pyridine and a portion of the xylene were distilled off. The ethoxylated trimethylol propane succinate is removed from the xylene by cooling and collected using a separatory funnel. The ethoxylated trimethylol propane succinate is redissolved in 50 mL of dichloromethane and stored overnight at −20° C. to recrystallize excess succinic anhydride. The crystals were filtered off and dichloromethane is added to prepare a volume of 200 mL. N-hydroxysuccinimide (7.8 g, Aldrich) and diisopropylcarbodiimide (10.5 mL, Aldrich) were added sequentially. The reaction is allowed to proceed at room temperature about four hours. The urea is removed using vacuum filtration. The ethoxylated trimethylol propane succinimidyl succinate is recovered by precipitation in a large excess of hexane and collected using a separatory funnel. Residual organic solvents were removed using a vacuum oven.

EXAMPLE 2

Determination of Crosslinking Time

The crosslinker prepared in accordance with EXAMPLE 1 as well as a variety of other crosslinking agents were synthesized and evaluated to determine their crosslinking time in the laboratory. The crosslinkers evaluated included ethoxylated trimethylol propane 20/3 succinimidyl succinate (TMP-SS), ethoxylated pentaerythritol 15/4 succinimidyl succinate (PE-SS), 4-arm poly(ethylene glycol) 2k succinimidyl succinate (PEG 2k-SS), 4-arm poly(ethylene glycol) 10k succinimidyl succinate (PEG 10k-SS), and ethoxylated phloroglucinol 30/3 succinimidyl succinate (ePG-SS).

Each crosslinker is dissolved in an appropriate solvent at the desired concentration. Each crosslinker solution (100 microliters) is mixed with 350 microliters of porcine blood treated with EDTA. The crosslinking time, i.e. the time required for the solution to substantially solidify, is determined, and results of the crosslinking time are shown in Table 1 hereinbelow.

TABLE 1

| Crosslinker | Crosslinker Concentration | Solvent | Crosslinking Time (approximate) (min) |
|---|---|---|---|
| None | None | DMSO | >20 |
| None | None | 0.9% saline + 5% NLS | >20 |
| PE-SS | 125 mg/mL | DMSO | 9 |

TABLE 1-continued

| Crosslinker | Crosslinker Concentration | Solvent | Crosslinking Time (approximate) (min) |
|---|---|---|---|
| PE-SS | 250 mg/mL | DMSO | 7 |
| PE-SS | 375 mg/mL | DMSO | 5.5 |
| PE-SS | 500 mg/mL | DMSO | 3 |
| PE-SS | 125 mg/mL | 0.9% saline + 5% NLS | >20 |
| PE-SS | 250 mg/mL | 0.9% saline + 5% NLS | >20 |
| PE-SS | 375 mg/mL | 0.9% saline + 5% NLS | >20 |
| PE-SS | 500 mg/mL | 0.9% saline + 5% NLS | >20 |
| TMP-SS | 125 mg/mL | DMSO | >20 |
| TMP-SS | 250 mg/mL | DMSO | >20 |
| TMP-SS | 375 mg/mL | DMSO | >20 |
| TMP-SS | 500 mg/mL | DMSO | >20 |
| TMP-SS | 125 mg/mL | 0.9% saline + 5% NLS | 10.5 |
| TMP-SS | 250 mg/mL | 0.9% saline + 5% NLS | 7.5 |
| TMP-SS | 375 mg/mL | 0.9% saline + 5% NLS | 5 |
| TMP-SS | 500 mg/mL | 0.9% saline + 5% NLS | 6 |
| PEG 2k-SS | 125 mg/mL | DMSO | 7.75 |
| PEG 2k-SS | 250 mg/mL | DMSO | 5 |
| PEG 2k-SS | 375 mg/mL | DMSO | 2.75 |
| PEG 2k-SS | 500 mg/mL | DMSO | 2.25 |
| PEG 2k-SS | 100 mg/mL | 0.9% saline + 5% SDS | 2 |
| PEG 2k-SS | 200 mg/mL | 0.9% saline + 5% SDS | 2 |
| PEG 2k-SS | 300 mg/mL | 0.9% saline + 5% SDS | 2 |
| PEG 2k-SS | 400 mg/mL | 0.9% saline + 5% SDS | 1.5 |
| PEG 10k-SS | 125 mg/mL | DMSO | >10 |
| PEG 10k-SS | 250 mg/mL | DMSO | 8 |
| PEG 10k-SS | 375 mg/mL | DMSO | 6 |
| PEG 10k-SS | 500 mg/mL | DMSO | 5 |
| PEG 10k-SS | 125 mg/mL | 0.9% saline + 5% NLS | 5 |
| PEG 10k-SS | 250 mg/mL | 0.9% saline + 5% NLS | 1 |
| PEG 10k-SS | 375 mg/mL | 0.9% saline + 5% NLS | 1 |
| PEG 10k-SS | 500 mg/mL | 0.9% saline + 5% NLS | >10 |
| ePG-SS | 125 mg/mL | DMSO + 5% Triton X-100 | 5 |
| ePG-SS | 250 mg/mL | DMSO + 5% Triton X-100 | 5 |
| ePG-SS | 375 mg/mL | DMSO + 5% Triton X-100 | 4 |
| ePG-SS | 500 mg/mL | DMSO + 5% Triton X-100 | 3.5 |

The above experimentation demonstrated that TMP-SS, PEG 2k-SS, and PEG 10k-SS were determined to be suitable crosslinkers for use in accordance with the methods and systems of the present invention.

EXAMPLE 3

Compressive Strength of Crosslinked Mass

In this example, a variety of crosslinkers are synthesized and evaluated to determine their compressive strength in the laboratory. These crosslinkers include ethoxylated trimethylol propane 20/3 succinimidyl succinate (TMP-SS), ethoxylated pentaerythritol 15/4 succinimidyl succinate (PE-SS), 4-arm poly(ethylene glycol) 2k succinimidyl succinate (PEG 2k-SS), 4-arm poly(ethylene glycol) 10k succinimidyl succinate (PEG 10k-SS), and ethoxylated phloroglucinol 30/3 succinimidyl succinate (ePG-SS).

Each crosslinker is dissolved in an appropriate solvent at the desired concentration, for example in accordance with EXAMPLE 2 hereinabove. Each crosslinker solution (1 mL) is mixed with 3.5 mL of porcine blood treated with EDTA. The mixture is placed in a 3-cc syringe (Becton Dickinson) and allowed to solidify for about 30 minutes at about 37° C. The Luer fitting is cut off the syringe using a razor blade, and the crosslinked mass is expelled from the syringe and placed into a 15 cc centrifuge tube filled with 0.9% saline. The mass is stored overnight at room temperature. Following the incubation, the mass is cut into sections about 8.5 mm long and loaded between two platens on an Instron 5543 compression assembly. The Instron compressed the synthetic thrombus at a rate of 15 mm/min until failure. Stress and strain data is collected and is provided in TABLE 2.

TABLE 2

| Crosslinker | Crosslinker Concentration | Solvent | Stress @ 12% Strain (psi) | Stress @ 29% Strain (psi) | Stress @ 59% Strain (psi) |
|---|---|---|---|---|---|
| None | None | DMSO | N/A | N/A | N/A |
| None | None | 0.9% saline + 5% NLS | N/A | N/A | N/A |
| TMP-SS | 125 mg/mL | 0.9% saline + 5% NLS | N/A | N/A | N/A |
| TMP-SS | 250 mg/mL | 0.9% saline + 5% NLS | 0.1 | 0.1 | 0.4 |
| TMP-SS | 375 mg/mL | 0.9% saline + 5% NLS | 0.1 | 0.1 | 0.4 |
| TMP-SS | 500 mg/mL | 0.9% saline + 5% NLS | 0.1 | 0.1 | 0.5 |
| PEG 2k-SS | 100 mg/mL | 0.9% saline + 5% SDS | 0.1 | 0.1 | 1.6 |
| PEG 2k-SS | 200 mg/mL | 0.9% saline + 5% SDS | 0.1 | 0.2 | 1.7 |
| PEG 2k-SS | 300 mg/mL | 0.9% saline + 5% SDS | 0.7 | 2.9 | 15.1 |
| PEG 2k-SS | 400 mg/mL | 0.9% saline + 5% SDS | 1.5 | 6.2 | 24.4 |
| PEG 10k-SS | 125 mg/mL | DMSO | 0.5 | 0.2 | 1.0 |
| PEG 10k-SS | 250 mg/mL | DMSO | 0.5 | 1.1 | 6.5 |
| PEG 10k-SS | 375 mg/mL | DMSO | 0.3 | 1.9 | 10.5 |
| PEG 10k-SS | 500 mg/mL | DMSO | 0.1 | 2.1 | 10.8 |
| PEG 10k-SS | 125 mg/mL | 0.9% saline + 5% NLS | N/A | N/A | N/A |
| PEG 10k-SS | 250 mg/mL | 0.9% saline + 5% NLS | 0.1 | 0.2 | 1.4 |
| PEG 10k-SS | 375 mg/mL | 0.9% saline + 5% NLS | 0.4 | 1.3 | 6.3 |
| PEG 10k-SS | 500 mg/mL | 0.9% saline + 5% NLS | 0.5 | 1.9 | 10.3 |

TABLE 2-continued

| Crosslinker | Crosslinker Concentration | Solvent | Stress @ 12% Strain (psi) | Stress @ 29% Strain (psi) | Stress @ 59% Strain (psi) |
|---|---|---|---|---|---|
| ePG-SS | 125 mg/mL | DMSO + 5% Triton X-100 | 0.2 | 0.8 | 4.6 |
| ePG-SS | 250 mg/mL | DMSO + 5% Triton X-100 | 0.3 | 1.4 | 8.4 |
| ePG-SS | 375 mg/mL | DMSO + 5% Triton X-100 | 0.4 | 1.6 | 10.0 |
| ePG-SS | 500 mg/mL | DMSO + 5% Triton X-100 | 0.4 | 1.7 | 11.9 |

The above experimentation demonstrated that PEG 2k-SS, PEG 10k-SS, and ePG-SS were suitable crosslinkers for the formation of a substantially solid mass in accordance with methods and systems of the present invention.

EXAMPLE 4

Durability of Crosslinked Mass

The durability of the crosslinked substantially solid mass is tested in a flow model simulating the flow dynamics of sidewall aneurysms. The crosslinking agent is prepared as a solution by adding TSAT (50 mg, Pierce) to 1 mL dimethylsulfoxide. 100 microliters of the crosslinker solution is added to 350 microliters of the EDTA-treated porcine blood and mixed. The crosslinker solution is injected into a 6 mm sidewall, silicone aneurysm and allowed to crosslink for 20 minutes. The aneurysm is placed in the flow model and phosphate buffered saline is pumped through the parent artery of the aneurysm at a flow rate of 300 mL/min, a temperature of 37° C., and a pressure of 120/80 mm Hg. The mass is found to be stable under these conditions in excess of 16 hours.

Next, the durability of the substantially solid mass is tested in a flow model simulating the flow dynamics of bifurcation aneurysms. The crosslinker solution is prepared as indicated hereinabove, by adding TSAT (50 mg, Pierce) to 1 mL dimethylsulfoxide. Thereafter, 100 microliters of the crosslinker solution is added to 350 microliters of the EDTA-treated porcine blood and mixed. The solution is injected into a 5 mm bifurcation, silicone aneurysm and allowed to crosslink for 20 minutes. The aneurysm is placed in the flow model and phosphate buffered saline is pumped through the parent artery of the aneurysm at a flow rate of 300 mL/min, temperature of 37° C., and pressure of 120/80 mm Hg. The synthetic clot is stable under these conditions in excess of 2 hours.

EXAMPLE 5

Formation of Crosslinked Mass in an Experimental Aneurysm

Experimental aneurysms are formed in rabbits by isolation and elastase digestion of the right common carotid artery in accordance with the method described by Cloft, et al., *Radiology*, 213: 223–228 (1999). The aneurysm is allowed to mature for about 6 weeks before being treated in accordance with a method of the present invention.

At the time of treatment, the aneurysm measured to be about 3 mm by about 8 mm. Through a femoral sheath, a microcatheter (Rebar Microcatheter, Micro Therapeutics, Inc., Irvine, Calif.) is positioned inside the aneurysm. A three-way stopcock is attached to the hub of the Rebar. A rotational hemostasis valve is attached to the three-way in line with the length of the microcatheter. A one-way stopcock is attached to the side port of the rotational hemostasis valve. The air is purged from the apparatus using saline. A mixing coil is positioned in the rotational hemostasis valve proximal to the three-way stopcock. A 4 mm×10 mm balloon catheter (e.g., HyperGlide, MicroTherapeutics, Inc., Irvine, Calif.) is positioned at the neck of the aneurysm.

The microcatheter is successively flushed with heparinized saline (several milliliters) and methylpyrrolidinone (0.35 mL). The crosslinker solution is 190 mg/mL ethoxylated pentaerythritol 15/4 succinimidyl glutarate in methylpyrrolidinone. The microcatheter is filled with the crosslinker solution. The balloon is inflated to seal the aneurysm neck. The crosslinker solution is introduced into the aneurysm sac concurrent with the mixing coil. The mixing coil is deployed, removed, deployed, and removed from the aneurysm sac to mix the crosslinking solution and the blood in situ. After five minutes, the balloon is deflated.

Digital subtracted angiography showed that the aneurysm sac is almost completely (i.e. 95%) occluded. Follow-up angiography two weeks post-treatment demonstrated near total occlusion of the aneurysm sac. Histological evaluation showed an unorganized blood clot largely filled the aneurysm sac. Virtually no inflammation is present.

The invention has been described herein with reference to certain examples and embodiments only. No effort has been made to exhaustively describe all possible examples and embodiments of the invention. Indeed, those of skill in the art will appreciate that various additions, deletions, modifications and other changes may be made to the above-described examples and embodiments, without departing from the intended spirit and scope of the invention as recited in the following claims. It is intended that all such additions, deletions, modifications and other changes be included within the scope of the following claims.

What is claimed is:

1. A method for treating a defect in a vascular structure, said vascular structure having a lumen and a wall, said method comprising the steps of:
    A) introducing a crosslinking agent into the defect such that the crosslinking agent becomes combined with blood within the defect; and
    B) allowing the crosslinking agent to react with blood to form a substantially solid mass within the defect.

2. The method according to claim 1 wherein Step A comprises i) inserting a catheter into the defect and ii) introducing the crosslinking agent through the catheter and into the defect.

3. The method according to claim 1 wherein Step A comprises i) inserting a catheter into the defect, ii) substantially sealing the defect to substantially entrap a quantity of blood within the defect and iii) introducing the crosslinking agent through the catheter and into the defect such that the crosslinking agent will combine with blood that is substantially entrapped within the defect.

4. The method according to claim 3 wherein the step of substantially sealing the defect to entrap a quantity of blood within the defect comprises positioning a blocking member adjacent to the defect to substantially seal the defect thereby entrapping a quantity of blood within the defect.

5. The method according to claim 4 further comprising the step of removing the blocking member after the crosslinking agent has been introduced into the defect.

6. The method according to claim 3 further comprising the step of removing the catheter after the crosslinking agent has been introduced into the defect.

7. The method according to claim 1 wherein the vascular defect comprises an aneurysm.

8. The method according to claim 1 wherein the vascular defect comprises a cerebral aneurysm.

9. The method according to claim 1 wherein the crosslinking agent reacts with proteins in the blood.

10. The method according to claim 1 wherein the defect comprises an arterio-venous malformation.

11. The method according to claim 1 wherein the defect comprises a cut, tear, perforation or other opening in the wall of the vascular structure.

12. The method according to claim 1 wherein the vascular defect has an inner cavity and an opening that extends through the wall of the vascular structure such that at least some blood flowing through the lumen of the vascular structure may enter the inner cavity of the defect through said opening.

13. The method according to claim 12 wherein Step B comprises i) substantially blocking the opening such that a quantity of blood is substantially entrapped within the inner cavity of the defect and, thereafter, ii) introducing the crosslinking agent into the defect such that the crosslinking agent becomes combined with blood that has been substantially entrapped within the defect.

14. The method according to claim 12 wherein Step B comprises i) inserting a catheter through the opening and into the inner cavity of the defect, ii) substantially blocking the opening such that a quantity of blood is substantially entrapped within the inner cavity of the defect and the catheter remains inserted into the inner cavity of the defect and iii) introducing the crosslinking agent through the catheter and into the defect such that the crosslinking agent becomes combined with blood that has been substantially entrapped within the defect.

15. The method according to claim 13 wherein the step of substantially blocking the opening comprises positioning a blocking member adjacent to the opening to substantially seal the opening thereby entrapping a quantity of blood within the inner cavity of the defect.

16. The method according to claim 15 further comprising the step of removing the blocking member after the crosslinking agent has been introduced into the defect.

17. The method according to claim 15 further comprising the step of removing the catheter after the crosslinking agent has been introduced into the defect.

18. The method according to claim 4 wherein the step of positioning a blocking member comprises advancing an expandable blocking member through the lumen of the vascular structure to a position adjacent to the defect while the expandable blocking member is in a substantially unexpanded configuration, and thereafter, expanding the expandable member such that it substantially seals the defect thereby entrapping a quantity of blood within the defect.

19. The method according to claim 15 wherein the step of positioning a blocking member comprises advancing an expandable blocking member through the lumen of the vascular structure to a position adjacent to the opening while the expandable blocking member is in a substantially unexpanded configuration, and thereafter, expanding the expandable member such that it substantially blocks the opening thereby substantially entrapping a quantity of blood within the defect.

20. The method according to claim 18 or 19 wherein the blocking member is formed integrally of or attached to said catheter.

21. The method according to claim 18 or 19 wherein the blocking member is separate from the catheter.

22. The method according to claim 18 or 19 wherein the blocking member comprises a balloon.

23. The method according to claim 1 wherein the crosslinking agent comprises a compound, each molecule of said compound having at least two nucleophilic-reactive functional groups.

24. The method according to claim 23 wherein each molecule of the compound has at least three nucleophilic-reactive functional groups.

25. The method according to claim 1 wherein the crosslinking agent comprises a compound, each molecule of said compound comprising a core portion and a plurality of nucleophilic-reactive functional groups.

26. The method according to claim 25 wherein the core portion comprises a compound that is water soluble and has at least two chemical groups suitable for derivatization.

27. The method according to claim 25 wherein the core portion of the compound is a straight or branched, chiral or nonchiral, cyclic or noncyclic, small molecule.

28. The method according to claim 27 wherein:
the core portion is selected from; pentaerythritol, di(pentaerythritol), nitriloacetic acid, glycerol, ethylene glycol, trimethylol propane, di(trimethylol propane), polyacids, heptanedioic acid, octanedioic acid, hexadecanedioic acid, multi-functional aromatic compounds, phloroglucinol, 1,2,4-benzene triol and pyrogallol; and
each functional group is independently selected from; electrophilic groups, esters, N-hydroxysuccinimide esters, vinyl sulfones, N-ethyl maleimides, iodoacetamides, orthopyridyl disulfides, aldehydes, sulfonyl chloride, aryl halides, epoxides, active esters, carbonyldiimidazoles, nitrophenyl carbonates, tresylates, tosylates, mesylates, and isocyanates.

29. The method according to claim 27 wherein the small molecule is coupled to at least one branched or unbranched polymer.

30. The method according to claim 29 wherein the polymer is water soluble.

31. The method according to claim 30 wherein the polymer is selected from; poly(ethylene glycol), poly(ethylene oxide), poly(vinyl alcohol), poly(propylene glycol), poly(ethylene oxide)-co-poly(propylene oxide), poly(vinyl pyrrolidinone), poly(amino acids), dextrans, poly(ethyloxazoline), polysaccharides, proteins, glycosaminoglycans, and carbohydrates.

32. The method according to claim 1 wherein the crosslinking agent comprises at least one compound selected from; ethoxylated trimethylol propane succinimidyl succinate, ethoxylated pentaerythritol succinimidyl succinate, 4-arm poly(ethylene glycol) succinimidyl succinate, and ethoxylated phloroglucinol succinimidyl succinate.

33. The method according to claim 1 wherein the croslinking agent is radiopaque.

34. The method according to claim 1 wherein the crosslinking agent has magnetic properties that allow it to be imaged by magnetic resonance.

35. The method according to claim 1 wherein the crosslinking agent is combined with a solvent.

36. The method according to claim 35 wherein the solvent comprises a saline solution.

37. The method according to claim 35 wherein the solvent comprises dimethysulfoxide.

38. The method according to claim 1 wherein the crosslinking agent is combined with a visualization enhancing agent.

39. The method according to claim 38 wherein the visualization enhancing agent comprises a radiopaque material.

40. The method according to claim 39 wherein the radiopaque material is selected from; tantalum, barium and other heavy metals.

41. The method according to claim 38 wherein the visualization agent comprises a material having magnetic properties that allow it to be imaged by magnetic resonance imaging.

42. The method according to claim 41 wherein the material having magnetic properties that allow it to be imaged by magnetic resonance imaging is selected from; gadolinium and gadolinium-containing compounds.

43. The method according claim 1 wherein the crosslinking agent is combined with a surfactant.

44. The method according to claim 43 wherein the surfactant is selected from; N-lauroylsarcosine, lauryl sulfate, and Triton X-100.

45. The method according to claim 1 wherein the crosslinking agent is combined with a biologically active substance that is effective to enhance and/or modify a biological response within or near the defect.

46. The method according to claim 1 wherein the biologically active substance is selected from; therapeutic agents, drugs, prodrugs, pharmaceuticals, proteins, cells, genetically modified cells, growth factors, fibroblast growth factors, platelet derived growth factors, insulin like growth factor, bone morphogenic proteins, inhibins, growth differentiating factors, activins, epidermal growth factors, vascular endothelial growth factors, connective tissue activated peptides, osteogenic factors and fragments, analogs, derivatives of growth factors, autograft cells or tissue, allograft cells or tissue, xenograft cells or tissue, naturally occurring cells or tissue, genetically modified cells or tissue, differentiated cells, non-differentiated cells, cells that promote the formation or ingrowth of fibrous connective tissue, substances that promote the formation or ingrowth of fiberous connective tissue.

47. The method according to claim 1 wherein the crosslinking agent is dispersed or dissolved in a solvent and is further combined with at least one other of i) a visualization enhancing agent, ii) a surfactant and iii) a biologically active substance.

* * * * *